(12) United States Patent
Beden et al.

(10) Patent No.: US 8,852,135 B2
(45) Date of Patent: Oct. 7, 2014

(54) METHOD AND DEVICE FOR MONITORING THE INTRODUCTION OF SUBSTITUTION FLUIDS UPSTREAM OF DOWNSTREAM OF A DIALYZER OF FILTER

(75) Inventors: Josef Beden, Mainz-Kastel (DE); Itka Bado, Frankfurt (DE); Georg Verch, Wiesbaden (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 489 days.

(21) Appl. No.: 13/124,353

(22) PCT Filed: Oct. 8, 2009

(86) PCT No.: PCT/EP2009/007214
§ 371 (c)(1),
(2), (4) Date: Jun. 10, 2011

(87) PCT Pub. No.: WO2010/043331
PCT Pub. Date: Apr. 22, 2010

(65) Prior Publication Data
US 2011/0237997 A1    Sep. 29, 2011

(30) Foreign Application Priority Data
Oct. 14, 2008 (DE) .......................... 10 2008 051 541

(51) Int. Cl.
*A61M 1/34* (2006.01)

(52) U.S. Cl.
USPC ....... 604/6.09; 604/4.01; 604/5.01; 604/6.06; 210/600; 210/634; 210/644; 210/645; 210/646

(58) Field of Classification Search
None
See application file for complete search history.

(56) References Cited

U.S. PATENT DOCUMENTS 3,946,731 A * 3/1976 Lichtenstein ................... 604/66
4,702,829 A * 10/1987 Polaschegg et al. ........ 210/195.2
(Continued)

FOREIGN PATENT DOCUMENTS

| EP | 0 189 561 | 8/1986 |
| EP | 1 348 458 | 10/2003 |
| EP | 1 595 560 | 11/2005 |

OTHER PUBLICATIONS

PCT International Search Report for PCT/EP2009/007214 mailed on Feb. 25, 2010.
(Continued)

*Primary Examiner* — Tan-Uyen T Ho
*Assistant Examiner* — Eric Bryant
(74) *Attorney, Agent, or Firm* — Kenyon & Kenyon LLP

(57) ABSTRACT

A method is provided for monitoring the introduction of substitution fluids for an extra-corporeal blood processing device with an extra-corporeal blood circuit, comprising an arterial blood line, running from an arterial patient connection to a first chamber of a dialyzer or filter divided into said first chamber and a second chamber by a membrane and a venous blood line, running from the first chamber of the dialyzer or filter to a venous patient connection. A device is provided for monitoring the introduction of substitution fluids for an extra-corporeal blood processing unit with an extra-corporeal blood circuit and an extra-corporeal blood processing device with a device for monitoring the introduction of substitution fluids. The method and the device for monitoring the introduction of substitution fluids are based on monitoring the fluid level in the bubble trap, arranged in the venous blood line of the extra-corporeal blood circuit. The method and the device require that fluid is added to fill the extra-corporeal blood circuit, for example, for a rinsing procedure of the extra-corporeal blood circuit by means of the substitution fluid supply line arranged upstream or downstream of the dialyzer. A pre-dilution can be commanded when, after initiating the rinsing process the fill level in the bubble trap does not drop below a certain level. When by contrast the fill level drops below a given level a post-dilution can be commanded.

12 Claims, 1 Drawing Sheet

(56) References Cited

U.S. PATENT DOCUMENTS

| | | | |
|---|---|---|---|
| 5,702,597 A * | 12/1997 | Chevallet et al. | 210/195.2 |
| 5,858,239 A * | 1/1999 | Kenley et al. | 210/646 |
| 6,916,424 B2 | 7/2005 | Collins | |
| 7,316,662 B2 * | 1/2008 | Delnevo et al. | 604/6.16 |
| 7,850,856 B2 * | 12/2010 | Zhang et al. | 210/741 |
| 2005/0065459 A1 * | 3/2005 | Zhang et al. | 604/4.01 |
| 2005/0118059 A1 * | 6/2005 | Olsen et al. | 422/44 |
| 2006/0254982 A1 | 11/2006 | Kopperschmidt | |
| 2007/0118064 A1 * | 5/2007 | Ueda et al. | 604/6.09 |
| 2008/0086087 A1 * | 4/2008 | Spohn et al. | 604/151 |
| 2010/0237011 A1 * | 9/2010 | Ross et al. | 210/636 |

OTHER PUBLICATIONS

International Preliminary Report on Patentability for PCT/EP2009/007214 mailed on Apr. 28, 2011.

* cited by examiner

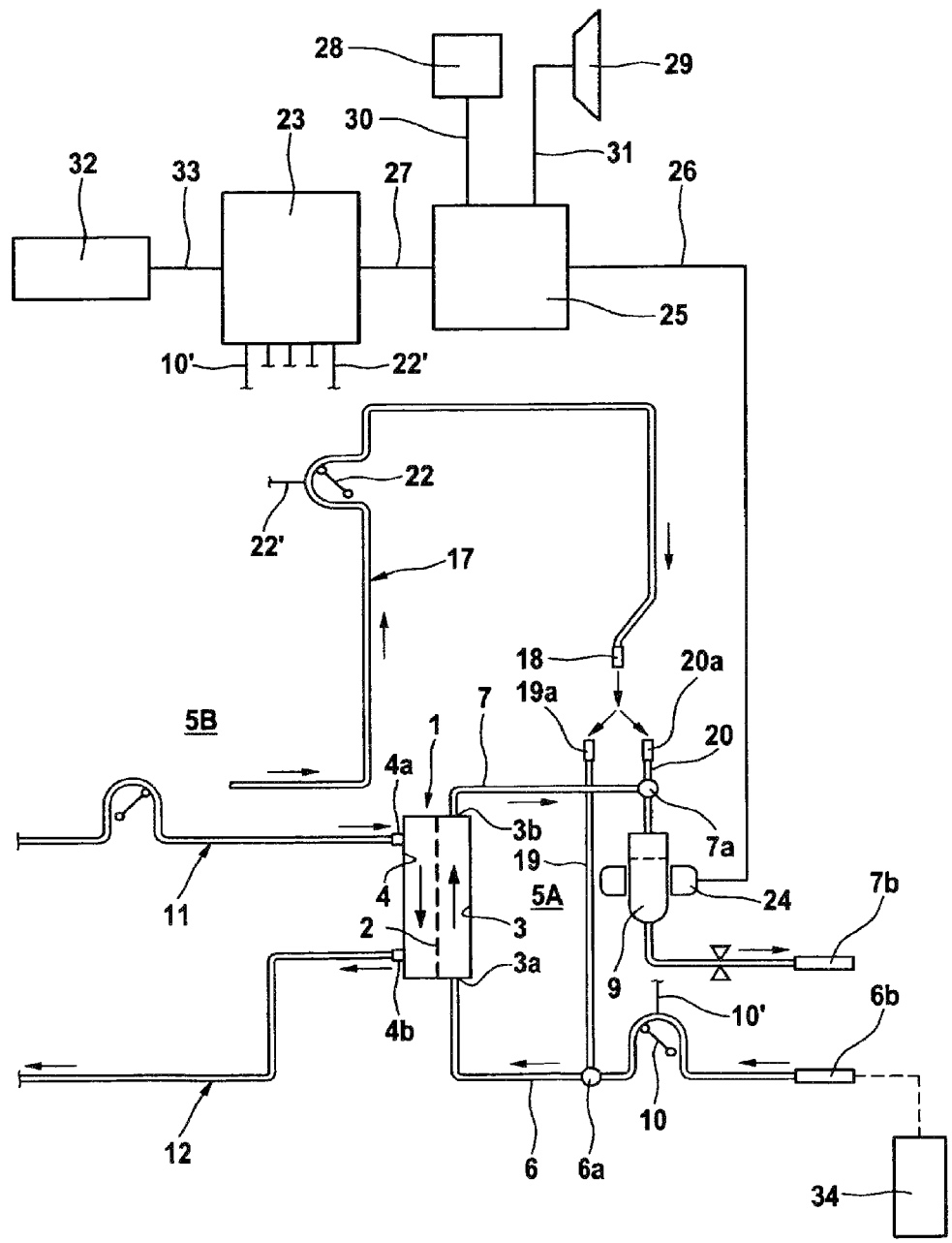

METHOD AND DEVICE FOR MONITORING THE INTRODUCTION OF SUBSTITUTION FLUIDS UPSTREAM OF DOWNSTREAM OF A DIALYZER OF FILTER

CROSS-REFERENCE TO RELATED APPLICATIONS

This application is the national phase of International Application No. PCT/EP09/007,214, filed Oct. 8, 2009, which claims foreign priority to GERMANY 10 2008 051 541.8, filed Oct. 14, 2008.

FIELD OF THE INVENTION

The present invention relates to a method for checking the supply of substitution fluid for an extracorporeal blood treatment apparatus in an extracorporeal blood circuit which comprises an arterial blood line, which leads from an arterial patient connection to a first chamber of a dialyzer or filter divided by a membrane into the first chamber and a second chamber, and a venous blood line, which leads from the first chamber of the dialyzer or filter to a venous patient connection. The present invention also relates to a device for checking the supply of substitution fluid for an extracorporeal blood treatment apparatus with an extracorporeal blood circuit as well as an extracorporeal blood treatment apparatus with a device for checking the supply of substitution fluid.

BACKGROUND

In order to remove substances usually eliminated with urine and for fluid withdrawal, various methods for extracorporeal blood treatment or cleaning are used in chronic kidney failure. In hemodialysis, the patient's blood is cleaned outside the body in a dialyzer. The dialyzer comprises a blood chamber and a dialyzing fluid chamber, which are separated by a semipermeable membrane. During the treatment, the patient's blood flows through the blood chamber. In order to clean the blood effectively from substances usually eliminated with urine, fresh dialyzing fluid flows continuously through the dialyzing fluid chamber.

Whereas the transport of the low-molecular substances through the membrane is essentially determined by the concentration differences (diffusion) between the dialyzing fluid and the blood in hemodialysis (HD), substances dissolved in the plasma water, in particular higher-molecular substances, are effectively removed in hemofiltration (HF) by a high fluid flow (convection) through the membrane of the dialyzer. In hemofiltration, the dialyzer functions as a filter. Hemodiafiltration (HDF) is a combination of the two processes.

In hemo(dia)filtration, part of the serum drawn off through the membrane is replaced by a sterile substitution fluid, which is fed to the extracorporeal blood circuit either upstream of the dialyzer or downstream of the dialyzer. The supply of substitution fluid upstream of the dialyzer is also referred to as pre-dilution and the supply downstream of the dialyzer as post-dilution.

In the known hemo(dia)filtration apparatuses, the substitution fluid is fed to the extracorporeal blood circuit from the fluid system of the machine via a substitution fluid line. With pre-dilution, the substitution fluid line leads to a connection point on the arterial blood line upstream of the dialyzer or filter, whereas with post-dilution the substitution fluid line leads to a connection point on the venous blood line downstream of the dialyzer. The substitution fluid line generally has a connector, with which it can be connected either to the venous or arterial blood line. In order to interrupt the fluid supply, a clamp or suchlike is provided on the substitution fluid line. A hemo(dia)filtration apparatus of this kind is known for example from European Patent Application Publication No. EP-A-0 189 561.

The monitoring of the blood treatment requires a knowledge of whether the substitution fluid is fed to the extracorporeal blood circuit upstream or downstream of the dialyzer or filter. European Patent Application Publication No. EP-A-1 348 458 describes a method and a device for monitoring the supply of substitution fluid for an extracorporeal blood treatment apparatus. The propagation time of the pressure waves of a substituate pump disposed in the substitution fluid line is measured for the detection of the supply of substitution fluid upstream or downstream of the dialyzer or filter. The supply of substitution fluid upstream or downstream of the dialyzer or filter is detected on the basis of the propagation-time measurement. The known method requires the use of a substituate pump generating pressure waves.

The blood treatment apparatus known from European Patent Application Publication No. EP-A-1 595 560 makes provision, for the detection of a pre- or post-dilution, to measure the pressure in the blood circuit downstream of the dialyzer or filter, whereby a pre- or post-dilution is detected on the basis of the change in the pressure after the switching-off and/or switching-on of the substituate pump provided for the delivery of the substitution fluid.

In practice, the pre- or post-dilution is preselected by the user by the fact that the substitution fluid line is connected either upstream of the dialyzer or filter to the arterial blood line or downstream of the dialyzer or filter to the venous blood line. Furthermore, the user preselects the treatment parameters required for the given blood treatment. There is a risk here that, after insertion of the hose system intended for one-off use, which comprises the arterial and venous blood line as well as the substitution supply line, the substitution supply line for a blood treatment with a pre-dilution is connected not to the arterial admission point, but rather to the venous admission point. Conversely, there is the risk that, for a post-dilution, the substitution line is connected not to the venous admission point, but rather to the arterial admission point. If the incorrect connection of the substitution line is not noticed, it can lead to considerable complications. In the case of a post-dilution with excessively high substitution flows, for example, it can lead to a high hemoconcentration and coagulation in the dialyzer or filter.

SUMMARY

An objective of the present invention is to provide a method which permits the checking of the supply of substitution fluid upstream or downstream of the dialyzer or filter of an extracorporeal blood treatment apparatus in a straightforward manner with a high degree of reliability. Furthermore, an objective of the present invention is to provide a device for checking the supply of substitution fluid upstream or downstream of the dialyzer or filter as well as an extracorporeal blood treatment apparatus which permits checking of the supply of substitution fluid upstream or downstream of the dialyzer or filter.

According to the present invention, the solution to these problems takes place with the features of the example embodiments disclosed herein.

The method according to the present invention and the device according to the present invention for checking the supply of substitution fluid are based on the monitoring of the fluid level in the bubble trap which is disposed in the venous blood line of the extracorporeal blood circuit. The method according to the present invention and the device according to the present invention require that the extracorporeal blood circuit is filled with a fluid. Filling of the extracorporeal blood circuit with a fluid is required especially when the blood circuit is to be rinsed. Since the arterial and venous blood line together with the dialyzer or filter are rinsed after the insertion of the blood hose system into the blood treatment apparatus generally before the start of the extracorporeal blood treatment, the filling of the extracorporeal blood circuit with the rinsing fluid does not represent an additional process step which would only be required for checking the supply of substitution fluid.

The method according to the present invention and the device according to the present invention are also based on the fact that fluid is fed to the extracorporeal blood circuit via the substitution supply line. If the extracorporeal blood circuit is filled with fluid via the substitution supply line upstream of the dialyzer or filter, the fluid can flow via the dialyzer or filter up to the bubble trap, so that this part of the blood circuit is completely filled with fluid. When the blood pump for conveying the fluid in the extracorporeal blood circuit is put into operation, the fluid level which has previously become established in the bubble trap does not fall. If, however, the fluid is fed to the extracorporeal blood circuit via the substitution supply line downstream of the dialyzer or filter, a large part of the hose system is not filled with fluid. The blood pump then conveys a corresponding volume of air into the bubble trap, so that the fluid level falls. It is then possible, therefore, to conclude that there is a pre-dilution if the fluid level does not fall below a predetermined level. If, on the other hand, the fluid level falls below a predetermined level, it can be concluded that there is a post-dilution.

When mention is made of a bubble trap in this context, a bubble trap is understood to mean any device which serves to free the blood flowing in the extracorporeal blood circuit from bubbles before the blood is fed to the patient.

The monitoring of the fluid level in the bubble trap can take place with the known monitoring devices. These are in any case present in the known blood treatment apparatuses.

In order to be able to distinguish reliably between a pre- and a post-dilution, a predetermined limiting value is preferably selected, below which the level must fall below the predetermined fluid level in order to conclude that there is a post-dilution. This thus prevents smaller fluctuations in the fluid level leading to false conclusions.

A preferred embodiment of the present invention makes provision such that the operational state of pre- or post-dilution is signalled. An optical and/or acoustic signal unit can be provided for this purpose.

A further preferred embodiment of the present invention makes provision such that an optical and/or an acoustic alarm is emitted if the operational state of pre- or post-dilution that has been preselected by the user is not detected. The operational state of pre- or post-dilution can for example be preselected by the user by the fact that the appropriate operational state is selected on a control unit. For this purpose, means can be provided on the control unit with which a pre- or post-dilution can be inputted, for example pushbuttons or switches. It is however also possible to preselect the operational state of pre- or post-dilution by stipulating specific parameters which are required for a blood treatment with a pre- or post-dilution.

The method according to the present invention and the device according to the present invention may be used with all treatment methods in which the patient's blood flows in an extracorporeal blood circuit.

An example of an embodiment of the present invention is explained below in greater detail by reference to the single drawing, which shows in a very simplified schematic representation an extracorporeal blood treatment apparatus together with a device for checking the supply of substitution fluid.

BRIEF DESCRIPTION OF THE DRAWINGS

The FIGURE shows a simplified schematic representation of the main components of a hemo(dia)filtration apparatus together with a device for checking the supply of substitution fluid into the extracorporeal blood circuit upstream or downstream of the dialyzer or filter.

DETAILED DESCRIPTION

When mention is made below of a dialyzer, this is also understood to mean a filter.

The hemo(dia)filtration apparatus comprises a dialyzer 1, which is separated by a semipermeable membrane 2 into a first chamber 3 through which blood flows and a second chamber 4 through which the dialyzing fluid flows. First chamber 3 is integrated into an extracorporeal blood circuit 5A, whilst second chamber 4 is incorporated into fluid system 5B of the hemo(dia)filtration apparatus.

Extracorporeal blood circuit 5A comprises an arterial blood line 6, which leads from an arterial patient connection 6b to inlet 3a of blood chamber 3, and a venous blood line 7, which leads from outlet 3b of blood chamber 3 of dialyzer 1 to a venous patient connection 7b. A venous bubble trap 9 (drip chamber) is incorporated into venous blood line 7 in order to eliminate air bubbles. The patient's blood is conveyed through the blood chamber of the dialyzer by means of an arterial blood pump 10, in particular a roller pump, which is disposed on arterial blood line 6.

Fluid system 5B comprises a dialyzing fluid supply line 11, which leads to inlet 4a of dialyzing fluid chamber 4, and a dialyzing fluid discharge line 12, which leads away from outlet 4b of dialyzing fluid chamber 4 of dialyzer 1. Fresh dialyzing fluid flows via dialyzing fluid supply line 11 out of a dialyzing fluid source (not represented) into the dialyzing fluid chamber, whilst the consumed dialyzing fluid is carried away from the dialyzing fluid chamber via dialyzing fluid discharge line 12 to a drain (not represented). The balancing device for balancing fresh dialyzing fluid against consumed dialyzing fluid which is generally provided in hemo(dia)filtration apparatuses is not represented for the sake of greater clarity. Additional devices for cleaning and rinsing the system are likewise not represented.

Fluid system 5B also comprises a substitution fluid supply line 17, which leads to extracorporeal blood circuit 5A. During the dialysis treatment, substitution fluid can be fed from fluid system 5B via substitution fluid supply line 17 to extracorporeal blood circuit 5A. Substitution fluid line 17 can be connected by connector 18 to a connection line 19 leading to arterial blood line 6 or to a connection line 20 leading to venous blood line 7. Connection lines 19, 20 possess suitable connection pieces 19a, 20a for this purpose.

The substitution fluid is conveyed by means of an occlusion pump, in particular roller pump 22, into which substitution fluid line 17 is inserted.

Blood pump 10 and substituate pump 22 are connected via control lines 10', 22' to a central control and regulating unit 23, from which the individual components are controlled taking account of the preselected treatment parameters.

The device for checking the supply of substitution fluid upstream or downstream of dialyzer 3 may form an independent unit, but may also be a component of the blood treatment apparatus. Since individual components of the device for detecting pre- or post-dilution are in any case present in the known blood treatment apparatuses, the device for detecting a pre- or post-dilution may simply be integrated into the known blood treatment apparatuses.

The device for checking the supply of substitution fluid comprises a monitoring device 24 for monitoring the fluid level in drip chamber (bubble trap) 9 and an evaluation device 25, which is connected via a data line 26 to monitoring device 24. Evaluation device 25 is in turn connected by a data line 27 to central control and computing unit 23.

Moreover, the device for checking the supply of substitution fluid comprises a signal unit 28 and an alarm unit 29, which are connected to evaluation device 25 via data lines 30, 31.

The treatment parameters required for the blood treatment are inputted on an input unit 32, for example a keyboard and/or an arrangement of switches and pushbuttons. Input unit 32 is connected to central control and regulating unit 23 via a data line 33.

The mode of functioning of the device for checking the supply of substitution fluid is described in detail below.

In order to perform the extracorporeal blood treatment, the required treatment parameters are first inputted on input unit 32, said parameters being processed by central control and regulating unit 23. The user may stipulate, amongst other things, whether the blood treatment is to be carried out with a pre-dilution or a post-dilution. This preselection of a pre- or post-dilution is read out from evaluation device 25.

The user now inserts the blood hose system, which comprises arterial and venous blood line 6, 7 and substitution supply line 17, into the hemo(dia)filtration apparatus. Depending on the selection of a pre-dilution or a post-dilution, the user must connect substitution fluid line 17 accordingly to connection line 19 or connection line 20.

Before commencement of the blood treatment, extracorporeal blood circuit 5A is rinsed. For this purpose, a bag 34 (represented solely in outline), which is filled with rinsing fluid, is connected to arterial patient connection 6b of arterial blood line 6. Blood pump 10 is then put into operation, which delivers rinsing fluid out of bag 34. Blood pump 10 is operated until such time as the line section of arterial blood line 6 lying upstream of arterial admission point 6a is completely filled with rinsing fluid. The blood pump is then stopped. Further filling of extracorporeal blood circuit 5A takes place with the substitution fluid via substitution supply line 17. For this purpose, substituate pump 22 is put into operation, which delivers substitution fluid via substitution supply line 17. Depending on the operational state of pre- or post-dilution, the substitution fluid flows either via arterial admission point 6a or venous admission point 7a into arterial or venous blood line 6, 7.

Substituate pump 17 is operated until such time as a predetermined fluid level has become established in drip chamber 9, said level being monitored with monitoring device 24. Once the predetermined fluid level has been reached, monitoring device 24 generates a signal which causes central control and regulating unit 23 to stop substituate pump 22. Blood pump 10 can now once again be put into operation in order to rinse the extracorporeal blood circuit. The fluid level of the drip chamber is monitored during the rinsing process.

If the user has preselected the operational state of pre-dilution, the fluid level in drip chamber 9 must not fall below a defined limiting value after blood pump 10 has been switched on, since extracorporeal blood circuit 5A has previously been completely filled with fluid via substitution supply line 17 connected to arterial admission point 6a. If, however, the user has connected substitution supply line 17 not to arterial blood line 6, but to venous blood line 7, i.e. has connected connector 18 not to 19a, but to 20a for the operational state of pre-dilution, the hose system has not been completely filled with fluid, since the substitution fluid has then been fed not upstream of dialyzer 3, but rather downstream of the dialyzer. In this case, the fluid level in drip chamber 9 falls, because the air volume that is enclosed in the line section of arterial blood line 6 downstream of arterial admission point 6a and the line section of venous blood line 7 upstream of venous admission point 7a and the dialyzer passes into drip chamber 9 after switching-on of blood pump 10.

Monitoring device 24 compares the predetermined fluid level with a reference value. If the difference between the predetermined fluid level and the reference value is greater than a predetermined limiting value, i.e. the fluid level has fallen by a predetermined value, monitoring device 24 generates a signal which is received by evaluation device 25. Alarm unit 29 then emits an acoustic and/or optical alarm, which signals to the user that he has connected the hose system incorrectly. Evaluation device 25 may also generate a signal which causes central control and regulating unit 23 to interrupt the operation of the dialysis apparatus.

If, on the other hand, the user has preselected the operational state of post-dilution, the fluid level must fall when blood pump 10 is switched on to carry out the rinsing process, because in this case the air volume enclosed in the hose line sections passes into drip chamber 9 on account of the incomplete filling of the hose system via substitution supply line 17 connected to venous admission point 7a. Evaluation device 25 in this case generates an alarm signal if the fluid level does not fall by the predetermined limiting value. Alarm unit 29 then again generates an alarm.

It can be displayed on signal unit 28 whether the user has connected the hose system for a pre-dilution or a post-dilution. If monitoring device 24 detects a drop in the fluid level in drip chamber 9 during operation of blood pump 10 for the rinsing process, the operational state of post-dilution is displayed, whereas the operational state of pre-dilution is displayed if the fluid level in the drip chamber does not fall.

The invention claimed is:

1. A method for checking a supply of substitution fluid for an extracorporeal blood treatment apparatus that includes (a) an extracorporeal blood circuit having an arterial blood line, which leads from an arterial patient connection to a first chamber of a dialyzer or filter divided by a membrane into the first chamber of the dialyzer or filter and a second chamber, and a venous blood line, which leads from the first chamber of the dialyzer or filter to a venous patient connection, (b) a substitution fluid supply line configured to supply substitution fluid at an arterial admission point upstream of the dialyzer or filter, wherein substitution fluid is fed to the extracorporeal blood circuit for a pre-dilution, and/or at a venous admission point downstream of the dialyzer or filter, wherein substitution fluid is fed to the extracorporeal blood circuit for a post-dilution, (c) a blood pump configured to convey blood in the extracorporeal blood circuit, and (d) a bubble trap disposed in the venous blood line, comprising:

filling a part of the extracorporeal blood circuit that lies between the arterial patient connection and the arterial admission point of the extracorporeal blood circuit with a fluid;

feeding the fluid to the extracorporeal blood circuit via the substitution fluid line connected either to the arterial admission point or the venous admission point until a predetermined fluid level has become established in the bubble trap;

putting the blood pump configured to convey the fluid in the extracorporeal blood circuit into operation;

monitoring the fluid level in the bubble trap; and determining, based on the monitoring, that (a) there is a connection of the substitution fluid line to the arterial admission point when the fluid level in the bubble trap does not fall below the predetermined fluid level or (b) there is a connection of the substitution fluid line to the venous admission point when the fluid level in the bubble trap falls below the predetermined fluid level.

2. The method according to claim 1, wherein the filling the part of the extracorporeal blood circuit that lies between the arterial patient connection and the arterial admission point of the extracorporeal blood circuit with a fluid includes connecting a container filled with a fluid to the arterial patient connection and putting the blood pump configured to convey the fluid in the extracorporeal blood circuit into operation.

3. The method according to claim 2, wherein the arterial patient connection is connected to a bag filled with a rinsing fluid.

4. The method according to claim 1, wherein the operational state of pre-dilution is signaled if the fluid level in the bubble trap does not fall below the predetermined level or the operational state of post-dilution is signaled if the fluid level in the bubble trap falls below the predetermined level.

5. The method according to claim 1, wherein the operational state of pre-dilution is preselected for the extracorporeal blood treatment apparatus, an acoustic and/or optical alarm being emitted if the fluid level in the bubble trap falls below the predetermined level.

6. The method according to claim 1, wherein the operational state of post-dilution is preselected for the extracorporeal blood treatment apparatus, an acoustic and/or optical alarm being emitted if the fluid level in the bubble trap does not fall below the predetermined level.

7. A device for checking the supply of substitution fluid for an extracorporeal blood treatment apparatus, the extracorporeal blood treatment apparatus including (a) an extracorporeal blood circuit which comprises an arterial blood line that leads from an arterial patient connection to a first chamber of a dialyzer or filter divided by a membrane into the first chamber and a second chamber, and a venous blood line that leads from the first chamber of the dialyzer or filter to a venous patient connection, (b) a substitution fluid supply line for supplying substitution fluid at an arterial admission point upstream of the dialyzer or filter, at which point substitution fluid is fed to the extracorporeal blood circuit for a pre-dilution, and/or at a venous admission point downstream of the dialyzer or filter, at which point substitution fluid is fed to the extracorporeal blood circuit for a post-dilution, (c) a blood pump configured to convey blood in the extracorporeal blood circuit, (d) a bubble trap disposed in the venous blood line, and (e) a monitoring device configured to monitor the fluid level in the bubble trap, comprising:

an evaluation unit configured to cooperate with the monitoring device such that (a) the presence of a connection of the substitution fluid line to the arterial admission point is determined if the fluid level in the bubble trap does not fall below a predetermined level or (b) the presence of a connection of the substitution fluid line to the venous admission point is determined if the fluid level in the bubble trap falls below the predetermined level.

8. The device according to claim 7, further comprising an input unit configured for preselecting the operational state of pre-dilution or post-dilution for the extracorporeal blood treatment apparatus.

9. The device according to claim 8, further comprising a signal unit configured to (a) signal the operational state of pre-dilution if the fluid level in the bubble trap does not fall below the predetermined level or (b) signal the operational state of post-dilution if the fluid level in the bubble trap falls below the predetermined level.

10. The device according to claim 8, further comprising an alarm unit configured to cooperate with the input unit configured for preselecting the operational state of pre-dilution or post-dilution, in such a way that, when pre-dilution is preselected, an acoustic and/or optical alarm is emitted if the fluid level in the bubble trap falls below the predetermined level or, when post-dilution is preselected, an acoustic and/or optical alarm is emitted if the fluid level in the bubble trap does not fall below the predetermined level.

11. An extracorporeal blood treatment apparatus, comprising:

an extracorporeal blood circuit having an arterial blood line that leads from an arterial patient connection to a first chamber of a dialyzer or filter divided by a membrane into the first chamber and a second chamber, and a venous blood line that leads from the first chamber of the dialyzer or filter to a venous patient connection;

a substitution fluid supply line configured to supply substitution fluid at an arterial admission point upstream of the dialyzer or filter, at which point substitution fluid is fed to the extracorporeal blood circuit for a pre-dilution, and/or at a venous admission point downstream of the dialyzer or filter, at which point substitution fluid is fed to the extracorporeal blood circuit for a post-dilution;

a blood pump configured to convey blood in the extracorporeal blood circuit;

a bubble trap disposed in the venous blood line;

a monitoring device configured to monitor the fluid level in the bubble trap; and a device configured to check the supply of substitution fluid, the device including an evaluation unit configured to cooperate with the monitoring device such that (a) the presence of a connection of the substitution fluid line to the arterial admission point is determined if the fluid level in the bubble trap does not fall below a predetermined level or (b) the presence of a connection of the substitution fluid line to the venous admission point is determined if the fluid level in the bubble trap falls below the predetermined level.

12. The device according to claim 11, wherein the arterial and venous blood line are part of a hose system configured for one-off use, the hose system including the substitution fluid supply line.

* * * * *